United States Patent [19]

Kaufman

[11] 4,415,740

[45] Nov. 15, 1983

[54] METHOD FOR PREPARING A LACTONE REACTION PRODUCT

[75] Inventor: Benjamin J. Kaufman, Wappingers Falls, N.Y.

[73] Assignee: Texaco Inc., White Plains, N.Y.

[21] Appl. No.: 387,995

[22] Filed: Jun. 14, 1982

[51] Int. Cl.$^3$ .................. C07D 309/30; C07D 307/32
[52] U.S. Cl. .................................. 549/273; 549/323; 549/291
[58] Field of Search ........................ 549/273, 291, 323

[56] References Cited

U.S. PATENT DOCUMENTS

| | | | |
|---|---|---|---|
| 3,155,685 | 11/1964 | Prill et al. | 549/273 |
| 3,248,187 | 4/1966 | Bell | 44/63 |
| 3,997,569 | 12/1976 | Powell | 549/273 |
| 4,047,899 | 9/1977 | Powell | 44/63 |
| 4,153,616 | 5/1979 | Powell et al. | 549/273 |

OTHER PUBLICATIONS

M. F. Ansell et al., Chemical Society Journal, London (1963) pp. 2640–2644.

M. F. Ansell et al., Quarterly Reviews (1964), pp. 211–213.

Primary Examiner—Norma S. Milestone
Attorney, Agent, or Firm—Carl G. Ries; Robert A. Kulason; Robert Knox

[57] ABSTRACT

A method for preparing a lactone reaction product comprising reacting an alkenyl-succinic acid under substantially anhydrous conditions at elevated temperature ranging up to about 100° in the presence of an α carbon halogen substituted acetic acid. The α carbon halogen substituted acetic acid may have from one to three halogen substituents and has a pKa of less than 3.

3 Claims, No Drawings

METHOD FOR PREPARING A LACTONE REACTION PRODUCT

THE PRIOR ART

The use of certain lactones or lactone reaction products as rust and corrosion inhibitors in hydrocarbon oil compositions is well known. Lactone reaction products prepared, for example, from alkenyl-substituted succinic acid have been used with much success in hydrocarbon oil compositions. In addition, lactones including alkenyl-substituted lactone reaction products have within recent years been used as intermediates in the reaction with, for example, substituted and non-substituted N-alkyl amines to form various lubricating oil additives products.

Hereintofore, much effort has been expanded in discovering new methods for preparing a lactone reaction product from alkenyl-substituted succinic acid. Commonly assigned U.S. Pat. No. 3,997,569 discloses a method for preparing a lactone product from alkenyl-succinic acid in which a variety of mineral acids, such as sulfuric and perchloric acids; organic acids, such as p-toluene sulfonic acid hydrate; solid acid catalyst, such as sulfonic acid ion exchange resins; and boron trifluoride etherate, serve as protonating agents or lactone electron pair acceptors in the lactonization reaction process. The reaction is conducted under substantially anhydrous conditions at an elevated temperature ranging up to 100° C., and is continued until infrared radiation absorption of the reaction product demonstrates formation of alkenyl-substituted 5 and 6 membered lactone raction products, i.e., there are strong absorptions in the 5.6 and 5.78 micron regions.

The method as disclosed hereinabove, although efficiently producing a high yield of the desired product, suffers from one process drawback that has increased the cost and limited the use of the resultant lactone product: this is the case whether the product is used by itself or as an intermediate in further reactions. This problem, which has been solved by the instant application, has to do primarily with the kind of protonating agents and electron pair acceptors employed in the above discussed patent. Although representing an advance over lactonization methods used prior to the date of this patent, it has now been found that when, for example, sulfuric acid is used to catalyze the reaction that it is difficult and time consuming to separate this protonating agent from the reaction product. The same would also be true with some of the other previously discussed protonating agents and electron pair acceptors.

If left in the reaction product the sulfuric acid, as well as the other catalytic agents, would by its presence alone interfere with the use of the reaction product a reactant in succeeding reactions: a significant amount of the added reactant is wasted as it reacts with the sulfuric acid and not the lactone. Moreover, because of the many washings which are employed and required to remove the sulfuric acid from the lactone reaction product, the performance of the lactone reaction product itself may be adversely affected. Additionally, the instant method is inefficient in that the washed-away sulfuric acid is diluted to such an extent that it cannot be recovered and used for succeeding lactonization reactions. All of these problems with the prior art method prevented it from becoming more fully utilized in lactonization reactions.

In an intensive effort to overcome these shortcomings, a novel method has been unexpectedly and surprisingly found to solve the problems in the processes found in the prior art. According to this process, a catalyst has been found which efficiently catalyses the lactonization reaction and which can later can be substantially moved from the reaction product without a great expenditure of time or expense. This method, which constitutes the heart of the invention, relates to the use of an α carbon halogen substituted acetic acid as a protonating catalyst in the lactonization reaction. With this process, the α carbon halogen substituted acetic acid can be distilled off by heating the reaction product under conditions of reduced pressure at a sufficiently high temperature, up to 105° C., for a sufficient time, up to 5 hours.

SUMMARY OF THE INVENTION

The instant invention relates to the use of an α carbon halogen substituted acetic acid as a catalyst in the lactonization of alkenyl-succinic acids. The catalyst chosen, in addition to effectively catalyzing the reaction, must be distillable out from the reaction mixture, without affecting the functioning of the lactone reaction product when it is, for example, employed as an additive in lubricating oil compositions or as a reactant in a succeeding reaction. These catalysts promote the reaction of an alkenyl-succinic acid, in which the alkenyl radical has an average molecular weight ranging from 300 to 3000, under substantially anhydrous reaction conditions at an elevated temperature (up to 100° C.) until a substantial portion of the alkenyl-succinic acid has been converted to the lactone reaction product.

SPECIFIC EMBODIMENTS OF THE INVENTION

According to the method of this invention, the alkenyl-substituted succinic acid, in which the alkenyl radical has a molecular ranging from a 300 to 3000, is admixed with the catalyst: a α carbon halogen substituted acetic acid. After mixing, the temperature of the reaction mixture is then raised up to about 100° C. to promote lactone formation while in the reaction vessel substantially anhydrous reaction conditions are maintained. The reaction is continued under these conditions for sufficient time to effect conversion of a substantial portion of the reactant to a lactone reactant product. It is convenient to follow the process of the reaction by withdrawing samples during the reaction and subjecting them to infrared analysis. The formation of alkenyl substituted 5 and 6 membered ring lactone reaction products is shown by infrared analysis at the 5.66 and 5.78 micron regions. Thus, by utilizing the infrared analysis or corrolated reaction times, it is possible to assure conversion of a major portion or substantially all of the alkenyl-succinic acid to a lactone reaction product.

The alkenyl-succinic reactant employed in this process is represented by the following formula:

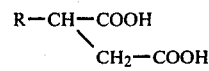

in which R represents an alkenyl radical having an average molecular weight ranging from about 300 to 3000. A more preferred reactant is alkenylsuccinic acid in which the alkenyl radical has an average molecular weight from about 700 to 2000. The most preferred reactants are those alkenyl-succinic acids in which the alkenyl radical has an average molecular weight ranging from about 800 to 1200.

It will be understood that the prescribed alkenyl-succinic acid reactant can be prepared from the corresponding alkenyl-succinic anhydride. Specifically, an alkenyl-succinic anhydride and water can be reacted in equal molar amounts to form the prescribed alkenyl-succinic acid reactant in accordance with known methods. Thus, the present invention contemplates that an alkenyl-succinic anhydride can be employed as a precursor to the reactant in this process by undergoing the hydrolysis reaction noted.

This process is also conveniently conducted by dissolving the prescribed alkenyl-succinic acid in an inert non-hydrating solvent such as a hydrocarbon solvent. A suitable solvent is a mineral oil having a SUS viscosity at 100° F. ranging from 50 to about 1000. Other suitable hydrocarbon solvents for this process include kerosene, benzene, xylene and the like.

The interesterification reaction or formation of a lactone reaction product in the present invention is conducted in the presence of an α carbon halogen substituted catalyst. The halogen substituents can be fluorine, chlorine, or bromine, and substitutions of from 1 to 3 positions on the α carbon of the acetic acid are contemplated. The substituents may be of one kind, for example, fluorine, or may be mixtures of the three possible halogen substituents, provided that the substituted acetic acid has a pKa below 3. If the pKa of the substituted acetic acid is above 3, the acid is not a sufficiently strong enough protonating agent to catalyze the lactonization reaction. Of great importance to this invention is the removal of the substituted acetic acid compounds from the reaction product mixture under conditions and time limits which will not adversely affect the efficiency of the overall process reaction: this is accomplished by conducting the distillation under subatmospheric conditions at a temperature of up to 95°–105° C. and for a time period of up to 5 hours. The substituted acetic acid will substantially distill off from the reaction mixture, leaving the reacted lactone product with a very small amount, if any, of the substituted acetic acid.

In cases where the lactone reactions product is employed as an intermediate in succeeding reaction, it is exceedingly important that there be no acid catalyst present in the reaction product mixture or if some is present, the acid is kept to minimal concentrations. If not, an acid such as sulfuric acid competes with the lactone product and often succeeds in reacting with the added reactant, such as, an amine, thus necessitating the need for more reactant to be added than if no amount of sulfuric acid is found in the mixture. It is therefore found under the present invention that using a substituted acetic acid offers an advantage: the resultant reaction product with no sulfuric acid present is a more preferred and efficient intermediate when used in succeeding reactions.

Suitable examples of halogen substituted acetic acid catalysts include those substituted acetic acid compounds having such halogen atoms as fluorine chlorine and bromide substituted onto the α carbon position to form mono-, di-, or tri-substituted acetic acids. Examples of these acetic acids includes, for example, mono-, di-, tri-fluoro acetic acid; mono-, di-, tri-chloro acetic acid; and mono-, di-,tri-bromo acetic acid. Also included within the scope of this invention are substituted acetic acid compounds in which more than one type of halogen atom is substituted onto the carbon. As examples of mixed halogen substituted acetic acids, the following are given: fluoro, chloro-α substituted acetic acid; chloro, bromo-α substituted acetic acid, and the like. All these described substituted acetic acids have a pKa of less than 3, and are, under the above prescribed conditions, distillable out of the reaction product mixture.

In employing the halogen substituted acetic acid, a sufficient amount should be added to the reaction mixture, before the start of the same, to provide from about 0.25 to 1.5 moles of protons per mole of the alkenyl-succinic acid. Preferably, an amount sufficient to provide from about 0.5 to 1 mole of protons is added to the reaction mixture. The preferred carbon substituted acetic acid is trifluroroacetic acid.

The reaction is normally conducted at a temperature from about 25° C. up to 100° C. with a temperature range from about 60° C. to <100° C. being especially suitable. A preferred temperature range with this process is from 70° C. to 98° C. Highly efficient conversions have been realized employing a temperature in the preferred range, namely from about 85° to 95° C. A temperature of 100° C. or above should be avoided because these temperatures tend to decrease conversion and lead to the production of undesirable reaction products.

For the production of high molecular weight alkenyl-substituted lactone reaction products of this invention, it is critical that the reaction be conducted under substantially anhydrous conditions. The reactant, solvent, and the catalyst must all be selected so as to insure substantially anhydrous and preferably essentially anhydrous reaction conditions. By substantially anhydrous conditions is meant the reaction mixture should contain no more than about 5% water. It is preferred that this mixture contain no more than 2% water with the most preferred situation being an essentially anhydrous reaction mixture.

It is to be understood that because the substituted acetic acid can be heated and distilled off from the mixture, the acid can be recycled and used in succeeding lactonization reactions. Under the distillation process hereinabove described, ordinarily over 90% of the original amount of acid employed can be recycled, thus saving a substantial amount of money and also increasing the efficiency of the system.

The following example illustrates the use of a catalyst system for the lactonization of an alkenyl-succinic anhydride which can be distilled off from the reacted product mixture.

EXAMPLE I

To 300 grams of polyisobutenyl succinic anhydride (containing 17% of unreacted polyisobutene of about 1290 to 1300 average molecular weight) was added a mixture of 2.2 grams (1.22 moles) of water and 3.5 grams (0.03 moles) of trifluoroacetic acid. The reaction was initiated and run for 4 hours at a temperature between 95° and 110° C. until infrared spectra indicated a high conversion to 5- and 6-membered ring lactones. After, the trifluoro- acetic acid was removed from the reacted product mixture by reduced pressure to yield the acid lactone reaction product. It took 3 hours of heating at a temperature of 95° to 105° C. until only trace amounts of trifluoroacetic acid remained in the acid lactone product mixture.

Based on the above, it can hereby be pointed out that this novel and unobvious lactonization process overcomes the problems hereintofore unsolved in the prior art; it does so in a highly efficient manner employing a catalyst, a carbon halogen substituted acetic acid, that is distilled substantially out from the reaction product (under conditions which do not affect the functioning of the product) collected, and, if desired, re-used in succeeding lactonization reactions.

What is claimed is:

1. A process for preparing an alkenyl-substituted lactone reaction product in which the employed catalyst initiates the reaction, and at the end thereof, is substantially removed from the product, which comprises the steps of admixing an alkenyl succinic acid, said alkenyl radical having an average molecular weight ranging from about 300 to 3000, with an alpha carbon halogen substituted acetic acid having from 1 to 3 halogen substituents and a pKa of less than 3, to form a substantially anhydrous reaction mixture and reacting said mixture at an elevated temperature up to about 100° C. until infrared spectra at about 5.66 and 5.78 microns indicates a substantial conversion of said alkenyl-succinic acid to said lactone reaction product, and heating the reaction product further at a temperature of from 95° C. to about 105° C. for about 1 to 5 hours to distill off the alpha carbon halogen substituted acetic acid from the reaction product to leave remaining an alkenyl-substituted lactone reaction product that is substantially free of halogen substituted acetic acid.

2. A method according to claim 1 wherein the halogen employed is selected from the group consisting of fluorine, chlorine and bromine.

3. A method according to claim 2 wherein the halogen carbon substituted acetic acid is trifluoroacetic acid.

* * * * *